United States Patent [19]

Nyilas et al.

[11] Patent Number: 4,670,286
[45] Date of Patent: Jun. 2, 1987

[54] METHOD OF FORMING PROSTHETIC DEVICES

[75] Inventors: Emery Nyilas, Austin, Tex.; Tin-Ho Chiu, Reading, Mass.

[73] Assignee: Allied Corporation, Morris Township, Morris County, N.J.

[21] Appl. No.: 813,336

[22] Filed: Dec. 26, 1985

Related U.S. Application Data

[62] Division of Ser. No. 533,877, Sep. 20, 1983, Pat. No. 4,594,407.

[51] Int. Cl.$^4$ .................... A61F 1/00; A61B 17/11
[52] U.S. Cl. .................................. 427/2; 623/1; 427/430.1
[58] Field of Search ............ 427/2, 430.1; 623/1

[56] References Cited

U.S. PATENT DOCUMENTS

| | | | |
|---|---|---|---|
| 3,272,204 | 9/1966 | Artandi | 623/66 |
| 3,425,418 | 2/1969 | Chvapil | 623/1 |
| 3,620,218 | 11/1971 | Schmitt | 623/1 |
| 3,883,901 | 5/1975 | Coquard | 623/1 |
| 4,032,993 | 6/1977 | Coquard | 623/1 |
| 4,074,366 | 2/1978 | Capozza | 623/1 |
| 4,137,921 | 2/1979 | Okuzumi | 623/1 |
| 4,208,511 | 6/1980 | Shalaby | 623/1 |

FOREIGN PATENT DOCUMENTS

WO80/02641 12/1980 PCT Int'l Appl. .

Primary Examiner—Sam Silverberg
Attorney, Agent, or Firm—Gale F. Matthews; Richard C. Stewart; Gerhard H. Fuchs

[57] ABSTRACT

A sterile shaped prosthetic device, suitable for insertion into a mammalian body, is at least partly composed of a bioresorbable material that is digestible by macrophages, its surface properties favor the attachment and adhesion of fibroblast cells capable of producing collagen for organized connective tissues, and the material itself or its degradation products can induce in vivo the formation of new capillary vessels (termed a "vasotropic" effect herein). Preferred prosthetic devices have through passages, the interspatial dimensions which are sufficient to permit several layers of mammalian cells to form within each passage. The invading fibroblast cells commence formation of collagen leading to connective tissue while macrophages and extracellular enzymes degrade the material, and newly formed capillary vessels penetrate the prosthesis and provide blood containing oxygen and nutrients which further the formation of organized tissue around as well as within the prosthetic device.

10 Claims, 5 Drawing Figures

METHOD OF FORMING PROSTHETIC DEVICES

This application is a division of application Ser. No. 533,877, filed Sept. 20, 1983, now U.S. Pat. No. 4,594,407.

This invention relates to prosthetic devices, and more particularly to prosthetic devices suitable for use in mammalian bodies in place of a part thereof.

Successful prosthetic devices of various shapes and applications have, in general, been made of materials relatively resistant to biodegradation such as stainless stell or inert biodurable polymeric materials. For example, replacement of injured, diseased, or nonfunctioning blood vessels has been conducted for many years, and nonresorbable synthetic permanent vascular grafts are currently made of either Dacron (R) (polyethylene terephthalate) or microporous Teflon (R) (polytetrafluoroethylene). Various prostheses such as grafts and bypasses for insertion into the vascular system must have certain properties including physical and mechanical compatibility with the vessel to which they are connected, suturability, conformability to contours, ability to withstand pressure and pressure fluctuations, and flexibility; biocompatibility—inlcuding such aspects as sterility and absence of toxicity, pyrogenicity, allergenicity, and mutagenicity; and adequate durability—both in terms of "shelf life" after fabrication and durability after implantation. Mechanical problems which can develop from mismatch of native vessel and prosthesis include elongation, kinking, aneurysm formation and anastomotic hyperplasia. Vascular prostheses made of biodurable materials have been so far the relatively most successful substrates, providing a conduit for maintaining continuous blood flow while inflicting preferably minimized and clinically tolerable hemotologic trauma. Most vascular grafts made of synthetic materials and in current clinical use are formed of knitted or woven nonbiodegradable fibers with open pores in the fabric which are typically closed by thrombosis (preclotting) before implantation. Such prostheses have been used both as vascular replacements and as bypass grafts but only with relatively larger arteries such as the abdominal aorta. While bioresorbable materials have been proposed for use in such prostheses, the practical uses of bioresorbable materials are, in general, currently limited to temporary devices such as fasteners (sutures and pins).

In accordance with one aspect of the invention, there is provided a sterile shaped prosthetic device suitable for insertion into a mammalian body, at least a portion of which is of a bioresorbable material. This material is digestible by macrophages, its surface properties favor the attachment and adhesion of fibroblast cells capable of producing collagen for organized connective tissues, and the material itself or its degradation products can induce in vivo the formation of new capillary vessels (termed a "vasotropic" effect herein). Preferred prosthetic devices have through passages, the interspatial dimensions which are sufficient to permit several layers of mammalian cells to form within each passage. The invading fibroblast cells commence formation of collagen leading to connective tissue while macrophages and extracellular enzymes degrade the material, and newly formed capillary vessels, penetrate the prosthesis and provide blood containing oxygen and nutrients which further the formation of organized tissue around as well as within the prosthetic device.

The term bioresorbable is used herein to mean not only biodegradable but that the degradation products, formed in vivo from those materials, are metabolizable as well by the mammalian body, without any toxic or otherwise harmful side effects. Also, as used herein, the term nonbioresorbability implies nonbiodegradability as well. It has been discovered that certain bioresorbable polyesters promote the regrowth of vascular tissues in and around a partially or completely metabolizable synthetic scaffold designed to lead to tissue organization that is comparable to intact native arterial vessels. These polyesters also exert a "vasotropic" effect in vivo by inducing the formation of new caillary vessels within surrounding tissues. The adjective "vasotropic" is used here with the intent to distinguish the effect which can be arbitrarily induced by synthetic materials, from the "angiogenic" effect or, "angiogenesis" that is a spontaneous phenomenon generally associated with the growth of malignant tissues.

In accordance with another feature, there is provided a vascular prosthesis that includes a sterilized flexible, tubular device of fabric scaffold structure, with at least 25 percent of the yarns of the fabric scaffold structure consisting solely of bioresorbable material in an arrangement such that, on implantation of the vascular prosthesis in a mammalian body, the bioresorbable material undergoes absorption and provides passages through the scaffold stucture that have interspacial dimensions sufficient to allow several layers of mammalian cells to form within each passage.

Surface properties of the bioresorbable material encourage not only the invasion of fibroblast cells onto and into the fabric of the vascular graft, but also encourage the attachment as well as the adhesion of fibroblast cells. Not only the shape of fibroblast cells but the incidence of their adhesion and attachment are a function of the surface properties of the porous substrate. Using wettability spectrum analysis, the surface properties of bioresorbable materials in accordance with an aspect of the invention are computable as well as characterizable in terms of the total surface free energy, $\gamma_s$, which can be expressed as the sum of $\gamma_s^d$ and $\gamma_s^p$, the dispersion (i.e., Van der Waals-London) force and the polar (i.e., hydrogen bonding, dipole-dipole, etc.) force components, respectively. Fibroblast cell attachment and adhesion is favored if (i) the total surface free energy of the prosthesis, $\gamma_s$ is in the range of 35–60 dyne/cm and preferably, in the range of 40–55 dyne/cm, and (ii) the dispersion force component, $\gamma_s^d$ is predominant, amounting to more than one-half of $\gamma_s$, and preferably constituting 60%–80% of $\gamma_s$.

The surface properties of the bioresorbable material also encourage the infiltration of the porous prosthesis by macrophages which are cells of the mammalian immune mechanism and are capable of digesting the material in bioresorbable vascular grafts, in accordance with the invention, the formation of organized collageneous tissue is part of the reconstructive processes ultimately leading to vascular wall tisue organization which is similar or, comparable to that of intact native arterial vessel walls.

Certain bioresorbable polyesters impart "vasotropic" properties to vascular grafts which are manifested in vivo by the induction of the formation of entirely new capillary blood vessels in living soft tissues. In the presence of a bioresorbable coating which is either composed of a single substance having "vasotropic" properties or, which has a component exhibiting "vasotropic"

properties, the induced formation of new capillary vessels penetrating the interstices of the graft occurs. In addition to vascular grafts, bioresorbable materials capable of exerting "vasotropic" effects either in the short or, in the long term can be of significant value by initiating, aiding or accelerating natural reconstructive processes, in both soft and hard damaged tissues of the mammalian body, which would otherwise not occur or, would take place only at slow rates as a result of inadequate transport of metabolites to and from the regeneration site. As a result of the formation of new capillary vessels or neovascularization, the transport of metabolites and oxygen needed for, at least, the partial reconstruction of damaged tissues becomes facilitated. The establishment of transport channels for nutrients can be especially significant where the damaged tissue had a relatively low level of original vascularization such as in bones or, the original vascularization of the tissues was destroyed or rendered nonfunctional such as in burnt soft tissues of the dermis and subdermal layers. Thus, for those familiar with the art, the spectrum of applicability of these bioresorbable vasotropic materials can involve intraosseous implants to aid the regrowth of missing bone segments after compound fractures, dental implants, and burn covers aiding, at least the partial, regeneration of devitalized subdermal layers until they become covered by epithelial cells.

An appropriate deposition of a bioresorbable coating generally smoothens the luminal blood-contacting surface of both woven and knitted fabric vascular grafts. In turn, this results in a smaller amount of deposits from blood (viz., platelets and fibrin) as on uncoated surfaces, ultimately leading to relatively thin pseudoneointimal and neointimal layers covering the luminal surface of the graft.

As a result of the formation of organized tissues within the interstices of the graft, as noted above, the adherence of pseudoneointimal and neointimal layers formed on the luminal surface does not only occur to the graft alone, but to the collageneous and connective tissues as well, which are organized within the graft interstices, irrespective of whether the fabric graft is made of either a bioresorbable or a nonbioresorbable material. Establishment of continuity in the biological material formed on the luminal side of the graft and the organized tissues formed within and on the outside surface of the graft are measures rendering a potential delamination of the luminal layer more difficult than when this continuity does not or cannot exist. Neointimal delamination is known to be one of the modes of failure of current nonbioresorbable vascular grafts.

To initiate, maintain and accomplish the processes of vascular wall reconstruction, bioresorbable coatings preferably exert their effects both in the short and in the long term. For example, the desired "vasotropic" properties might be imparted by means of a single substance which, however, undergoes bioresorption at a rapid rate. Another single substance might be less "vasotropic" than the former but its bioresorption rate in vivo is also less than that of the former. Thus, to maintain the vascular wall reconstructive processes both in the short and long term, a composite of both of these bioresorbable substances is more preferred as a coating than a single-component coating consisting only of either of the two substances.

Polyesters are, in general, constituted of a dicarboxylic acid and a diol, which are reacted with each other in a so-called condensation reaction with the elimination of water. Upon hydrolytic attack, the dicarboxylic acid and diol components are reconstituted with the uptake of water. Bioresorbable polyesters in accordance with the invention are derived from Krebs-Cycle dicarboxylic acids and diols that are also metabolizable. With respect to the known mechanisms of the mammalian body degrading carbon chains, namely, beta oxidation followed by chain scission, the diols incorporated into these polyesters preferably consist of an even number of carbon atoms (since chain scission occurs in pairs of carbon atoms), and the number of carbon atoms is greater than two. Thus, for the synthesis of our bioresorbable polyesters, diols such as 2,3-butanediol, 1,4-butanediol and 2,5-hexanediol, etc., are preferred.

Vascular grafts made completely either of nonresorbable (viz., Dacron) or bioresorbable yarns (i.e., polyglycolic acid), or grafts made using any combination of these yarn types (viz., partially resorbable grafts) can be coated with bioresorbable polyesters which are capable of eliciting the interstitial penetration of cells in vivo. This effect can be well considered to promote the integration as well as the stabilization of vascular prostheses. Since, in addition, some of these polyesters demonstrably exert a "vasotropic" effect, this can ultimately result in the ingrowth of capillary vessels or, vascularization of the graft.

As a result of their bioresorbability, the polyester graft coatings become degraded and ultimately vanish, gradually increasing the biological porosity of the graft over its initial porosity. The rate at which a given amount of bioresorbable coating becomes metabolized is a function of the mass of the coating applied, as well as of the molecular weight and structural characteristics of polyesters used. The mass of coating that is deposited over unit nominal area of graft surface has, among others, some practical limitations in order to preserve the compliance, conformability, flexibility, etc. of the woven or knitted fabric tubular structure while still sealing the interstitial pores of both types of fabric to the extent that sealing by graft preclotting is alleviated. In accordance with another aspect of the invention, depending on the type of fabric structure to be coated, the mass of the coating applied and the molecular structural characteristics of polyesters used, or a combination of both, may be utilized to control the in vivo longevity of the coating while simultaheously achieving the sufficient sealing of fabric porosity.

As a result of the generally greater yarn density of woven grafts (or their smaller porosity compared to knitted grafts), the mass of uniformly distributed coating required to seal these grafts without compromising the fabric's physical properties is typically on the order of 10 to 15 mg per unit nominal area of graft surface. For example, for an 8 mm woven graft measuring 10 cm in length, a total of about 200 to 250 mg of polyester coating is sufficient. Thus, for woven grafts, the mass of coating applied represents a secondary means of controlling the rate at which a bioresorbable coating is metabolized. Control over the in vivo longevity of woven-graft coatings is primarily exerted via the molecular structural characteristics of polyesters used.

In contrast to woven grafts, the porosity of knitted grafts, as measured by standard leak rate methods, is about one order of magnitutde greater (i.e., approx. 1,500 ml $cm^{-2} min^{-1}$ vs. 150 ml $cm^{-2} min^{-1}$). With the coating initially depositing on individual yarns, the total amount of coating which has to be deposited on a knitted graft until its interstitial volume becomes sealed by the coalescence of individual yarn coatings, is large enough to compromise the desirable conformability of this type of graft, converting it into a rigid pipe. Another aspect of the invention is to cause the polyester coating to spread over and form a film above the individual yarns of knitted grafts, without saturating their interstitial spaces and thereby preserving their desirable machanical properties. Under these film-forming conditions, the mass of uniformly distributed coating that is necessary to sufficiently seal knitted grafts is on the order of 35 to 45 mg per unit nominal area of graft surface. For the same 8 mm diameter 10 cm long but knitted graft, a total polyester coating of about 1.0 g is required. As a result of the relatively greater mass of coating taken up, this factor becomes significant to exerting control over the in vivo longevity of polyester coatings deposited on knitted grafts.

Independent of the different masses of coating required by different types of grafts, a feasible way of exerting control over the in vivo longevity of graft coatings is via the molecular structural characteristics of polyesters used. As discussed below, the rate of bioresorption of polyesters derived from Krebs-Cycle dicarboxylic acids can be influenced to the extent as to have these materials metabolized either within relatively short periods of time, i.e., four to six weeks, or over relatively long periods on the order of four to six months.

Preferred polyesters are, in general, homo- and copolyesters derived from succinic, L-hydroxysuccinic (or malic), and fumaric acids, as well as from 2,3-butanediol and 1,4-butanediol, and include poly(2,3-butylene succinate) and copoly(1:3 1,4-butylene/2,3-butylene succinate).

Poly(2,3-butylene succinate), shown below, is an amorphous homopolyester with a relatively low softening point

(45° to 50° C.) that has relatively "fast" in vivo bioresorption rates, with samples becoming completely metabolized in four to six weeks without any observable untoward effects.

The structure of a random copolyester, copoly(1:1 1,4-butylene/2,3-butylene succinate) is shown below

The adjective "random" is used for this copolyester because the sequence of 1,4- and 2,3-butylene moieties in the polyester backbone may not be necessarily monotonous throughout the entire length of polymer chains. A similar "hybridized" polymer with a relatively high 2,3-butylene moiety content, copoly(1:3 1,4-butylene/2,3-butylene succinate) has the good film-forming properties of the poly(2,3-butylene succinate) homopolymer but undergoes bioresorption at rates comparable to that of the (1,4-butylene succinate) homopolyester. Thus, in vivo bioresorption rates may be influenced via the nature of chain segments introduced by the diols.

Another homopolyester is poly(2,3-butylene fumarate) shown below

This homopolyester is an unsaturated analogue of poly(2,3-butylene succinate), has a moderately high softening point (75° to 85° C.), and its all-trans structure has been confirmed by NMR spectroscopy. Compared to the succinate, the subcutaneous bioresorption of the fumarate polyester is significantly slower under identical conditions, and is on the order of three to four months. The introduction of transdouble bonds into the polyester backbone represents another means to influence in vivo bioresorption rates.

Still another homopolyester is poly(2,3-butylene hydroxy succinate), its molecular structure being shown below As indicated by the asterisk, the hydroxy succinic acid moiety has an asymmetrically substituted, optically active carbon atom which allows for the use of either the L- or the D- stereoisomers, or the D,L-racemic mixture of the two enantiomorphs in the polyesters formed. Poly(2,3-butylene D,L-hydroxy succinate) is an amorphous substance with a moderately high softening point (75° to 80° C.). The bioresorption rate of this polyester is significantly slower than that of poly(2,3-butylene succinate) under identical conditions.

The synthesis of polyesters composed of Krebs-Cycle dicarboxylic acids and the diols specified generally involves a straightforward condensation reaction with the concurrent elimination of water. To obtain polyesters with adequate physical properties, however, the molecular weight of these polymers has to be sufficiently high (i.e., at least 10,000 Daltons or greater) or, preferably, the maximum achievable with a given dicarboxylic acid or diol.

To alleviate any potential catalyst-related physiologic effects or artifacts of unkown origin, the condensation reaction between Krebs-Cycle dicarboxylic acids and the selected diols is performed, at elevated temperatures (viz., 160° to 190° C.), with the vacuum-melt polymerization technique in the absence of any catalyst. Elevated temperatures and polymerization periods extending up to 72 or 96 hours are generally employed to attain polyester molecular weights in the range of 10,000 to 20,000 Daltons. To further assure the alleviation of any potential artifacts capable of obscuring the true in vivo biological effects of these polyesters, crude polymers are purified, at least twice, by reprecipitative fractionation before any biological application.

As a means of exerting control over the in vivo longevity of polyester coatings on vascular grafts, the weight-average molecular weight of polyesters is also of importance. In the absence of any catalyst and with increasing molecular weights, the rate of condensation reaction between a given dicarboxylic acid and diol gradually decreases such that a plateau molecular weight characteristic of this system is approached. If desired, further increases in weight-average molecular weight can be achieved by chain extension performed as follows.

The reactivity of different Krebs-Cycle dicarboxylic acids toward a given diol, HO—D1—OH, is different because the electronic structure of the acid residues is different and affects the reactivity of the carboxylic groups in different ways. For example, the reactivity of hydroxy succinic acid toward diols of interest is generally greater than that of succinic acid because of the activating effect of the alpha hydroxy group in the former. The activiating effect is independent of the stereochemical conformation of the hyroxy succinic acid, which can be either D-, or L- or the D,L racemate.

In the synthesis of a polyester which is desired for graft coating and which is formed from the Krebs-Cycle dicarboxylic acid HOOC—R1—COOH and the diol HO—D1—OH, a slight excess in the range of 5 to 10 mole percent of the diol is employed in the condensation reaction. This excess renders the polyester molecules formed to be overwhelmingly terminated by the alcoholic hydroxyl groups of the diol, HO—D1—OOC—R1—COO— ... —D1—OH. If the plateau value of the weight-average molecular weight that is attainable by the polyester under these conditions, is insufficient to meet in vivo graft coating longevity requirements, following its isolation, the hydroxy-terminated polyester can be subjected to chain extension by reacting it with small amounts of another Krebs-Cycle dicarboxylic acid, HOOC—R2—COOH which is more reactive than the dicarboxylic acid HOOC-R1—COOH. The chain-extension is also performed under the conditions of vacuum-melt polymerization at elevated temperatures, yielding essentially the same polyester but with substantially increased weight-average molecular weight, and with the general formula of HOOC—R2—COO—[—D1—OOC—R1— ... —D1-]—OOC—R2—COO—[D1—OOC—R1— ... —D1]— ... —R2—COOH where the bracketed chain segments correspond to the average molecular weight of the original polyester. For example, upon treatment under these conditions with 0.005% to 0.01% by weight of hydroxy succinic acid which was homogeneously dispersed in the melt of a hydroxy-terminated poly(2,3-butylene succinate) of 12,000 Daltons, the weight-average molecular weight of this polyester increased to 28,500 Daltons, as determined by gel permeation chromatography.

Particular embodiments of tubular vascular graft prostheses in accordance with the invention are composite structures of nonbioresorbable multifilament yarns in a fabric array with through passages that contain bioresorbable multifilament yarns. The fabric is woven or knitted in a desired fabric pattern (for example, either a helical or rectangular weave) and is of a desired porosity. The pores of the tubular scaffold of nonbioresorbable material have interspacial dimensions of about 200 microns dimensions, such that several layers of cells can form through and within each pore. An overcoating of a bioresorbable, vasotropic-effect inducing material having a coating thickness typically in the range of 15 to 25 microns may be used on some or all of the yarns or on the tubular structure itself.

Suitable bioresorbable yarns are composed of polyglycolic acid; polyglycolic acid/poly(D,L-lactic acid) random copolymers having any ratio between its glycolate and D,L-lactate moieties; polyglycolic acid/poly(L-lactic acid) random copolymers having any ratio between its glycolate and L-lactate moieties; poly(D,L-lactic acid) homopolymers in which the abundance of L-lactate moieties can comprise 50% to 99.99% of lactate moieties; and poly(L-lactic acid) stereospecific homopolymers. The homo- and copolymers named above are selected such as to impart, by means of their molecular structure, controllably variable rates of in vivo bioresorbability into the fibers and yarns made from them. Thus, one means of achieving the gradual bioresorption of the vascular graft scaffold is by interdigitation of yarns which exhibit, under identical conditions, different rates of bioresorption as a result of the particulars of their molecular structure. While absolute in vivo resorption rates vary according to the site of implantation in the mammalian body, under identical conditions, i.e., in identical implantation sites, the homopolymers, poly(glycolic acid) and stereospecific poly(L-lactic acid) undergo bioresorption at rates which are substantially slower than those of their copolymers: In general, copolymerization increases the rate of bioresorption. For example, poly(D,L-lactic acid) containing 50% or more of L-lactate moieties, is a copolymer of D- and L-lactic acids, and resorbs faster than the pure poly(L-lactic acid) homopolymer. Random copolymers of glycolic acid and D,L-lactic acid resorb faster than their corresponding homopolymers.

Other features and advantages of the invention will be seen as the following description of particular embodiments progresses, in conjunction with the drawings, in which.

DESCRIPTION OF PARTICULAR EMBODIMENTS

Figure 1:
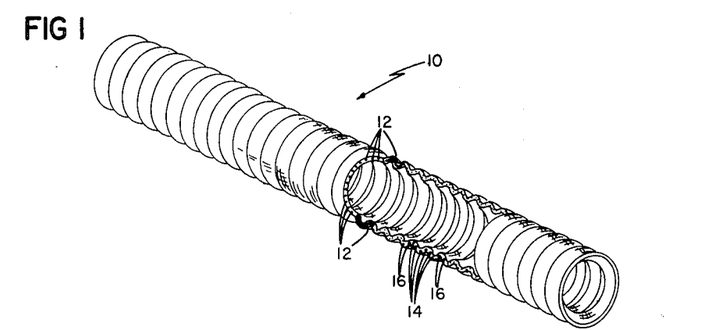
FIG. 1 is a perspective view (partially in section) of a tubular prosthesis in accordance with one embodiment of the invention.
Figure 2:
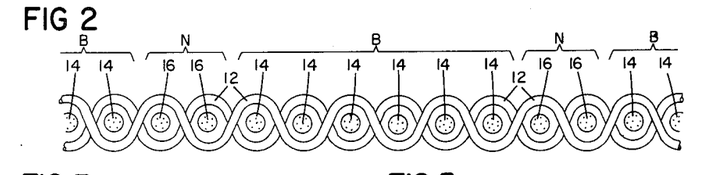
FIG. 2 is a diagram indicating the weave pattern employed in the prosthesis of FIG. 1.

The tubular vascular prosthesis 10 shown in FIG. 1 has a length of about five centimeters and is composed of nonbioresorbable (Dacron) multifilament longitudinal yarns 12 (each yarn 12 being approximately 150 microns in diameter and being composed of filaments about 20 microns in diameter) at a density of 100 yarns per inch, and multifilament bioresorbable (a 9:1 copolymer of PGA and poly(L-(-)-lactic acid) cross yarns 14 indigitated with nonbioresorbable (Dacron) multifilament cross yarns 16 a density of 100 yarns per inch—the cross-sectional diameter of the cross yarns 14, 16 and their filaments being the same as those of longitudinal yarns 12. The interdigitation of bioresorbable (B) cross yarns 14 with nonbioresorbable (N) cross yarns 16 is in yarn pairs with a resulting cross yarn pattern of NNBBBBBBNN . . . , as indicated diagrammatically in FIG. 2, providing a 75 percent bioresorbable cross yarn content. The tubular woven prosthesis had an internal diameter of six millimeter before crimping and a void area (or porosity) of about 18 percent. Crimping (a temperature-controlled process, without the use of any chemical agent) reached a depth of about one millimeter, which reduced the narrowest diameter of the prostheses before implantation to five millimeters. Control prostheses were made of Dacron polyfilament yarn of the same dimensions and using the same weaving technique.

After crimping, the bioresorbable and control prostheses were ultrasonicated in 0.1 percent aqueous solution of nonionic detergent (Triton X-100) for sixty minutes at room temperature and the vascular prostheses were then rinsed with pyrogen-free deionized water, followed by several rinses with 95 percent ethanol and drying in vacuo. The vascular prostheses were then packaged under a laminar flow hood equipped with high efficiency air filters and the packaged prostheses were subjected to standard ethylene oxide sterilization.

EXAMPLE 1

Under anesthesia, light anticoagulation and sterile operating room conditions, the vascular graft 10 was implanted by end-to-end anastomoses into the right external carotid artery of an adult sheep. Under identical conditions, an approximately five centimeter length of sterilized control graft consisting solely of woven Dacron multifilament yarns was implanted into the left external carotid artery of the same animal during the same operation.

After five weeks of indwelling time, both grafts were open to blood flow when the animal was anticoagulated and sacrificed by euthanasia, and the grafts were excised. The recovered graft with 75 percent bioresorbable cross yarn content remained patent, displayed on a smooth pseudoneointimal layer on its luminal blood-contacting surface, and showed a partial degradation of bioresorbable yarns and transmural interstitial vascularization.

EXAMPLE 2

Under the operative conditions described in Example 1, an approximately five centimeter long and five millimeter diameter piece of tubular partially bioresorbable prosthesis with a 75 percent bioresorbable cross yarn (polyglycolic acid multifilament) content—the other cross yarns and the longitudinal yarns were of multifilament Dacron—was implanted into the right external carotid artery of a sheep. Into the left external carotid artery of the sheep, a control prosthesis of all-Dacron, also of approximately five centimeters length, was implanted. Under conditions described in Example 1, the experimental animal was electively terminated after fifteen weeks. The recovered nonbioresorbable (all-Dacron) graft was occluded while the recovered bioresorbable graft remained patent, displayed smooth pseudoneointimal layers on its luminal blood-contacting surface, and displayed a partial degradation of bioresorbable yarns and transmural interstitial vascularization.

EXAMPLE 3

A 7.5 centimeter long piece of a human-implantable grade, crimped, woven Dacron DeBakey-type vascular graft having an eight millimeter diameter, was subjected to cleansing and sterilization as described in Example 1. Using a dipping apparatus which was enclosed in a dust-free chamber and had controllable speeds of vertical motion, the dried vascular graft was immersed, at a rate of about 0.5 centimeter per second, into a solution of five grams of double-precipitated poly(D,L-lactic acid) (approximately 70,000 Daltons weight-average molecular weight) and five grams of double-precipitated poly(2,3-butylene succinate) (approximately 17,500 Daltons weight-average molecular weight) in 100 milliliters of pure acetone. Following the first dip and a partial drying of the coating deposited, the vascular graft was inverted and redipped under the same conditions. After the second dip, the vascular graft was dried and packaged under a laminar flow hood equipped with high efficiency air filters, and the packaged prosthesis was subjected to standard ethylene oxide sterilization.

Figure 3:
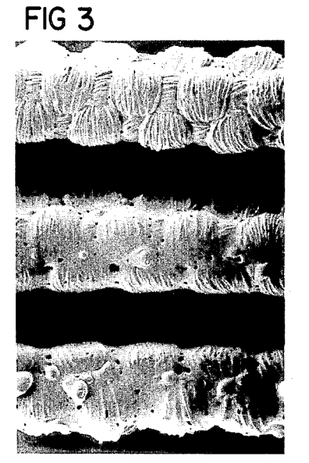
FIGS. 3 and 5 are a scanning electron micrographs of another embodiment of a vascular prosthesis in accordance with the invention.

FIG. 3 is a scanning electron micrograph (SEM) showing, at 50× magnification, the appearance of three ribs (or three crimpings) of the coated graft, which were taken from the end zone of the coated graft segment. On the ribs appearing at left and in center, the coating has covered the inter-yarn voids smoothening the surface. As determined from SEM's taken from cross sections, the thickness of the bioresorbable polyester composite coating was on the order of 15–25 microns. When deposited at this layer thickness, the coating filled the graft interstitial spaces to the extent that it did not only reduce the fraying of cut ends (a known propensity of grafts having this type of weave pattern), but it also eliminated the need for preclotting.

Under operative conditions described in Example 1, an approximately five centimeter piece of the coated vascular graft was implanted by end-to-end anastomoses into the right external carotid artery of an adult sheep. Under identical conditions, an approximately five centimeter piece of the same human-implantable Dacron graft which had not been treated or coated but only sterilized, was pre-clotted and implanted into the left external carotid artery of the same animal during the same operation. After five weeks of indwelling time, both grafts were open to blood flow when the animal was electively terminated under conditions described in Example 1, and the grafts were excised. On its luminal blood-contacting surface, the coated vascular graft had a smooth glistening pseudoneointimal layer virtually free of any red or white thrombotic deposit, whereas the same surface of the uncoated Dacron graft had a comparatively thick layer of adherent red and white thrombotic deposits. On its external surface, the coated Dacron had induced a significantly less severe tissue response and inflammatory reaction than the uncoated graft. Histopathology of segments taken from both grafts indicated a much stronger interstitial permeation of fibroblast cells into the coated graft.

Although a well-defined cause and effect relationship for this in vivo phenomenon has not yet been established, the attachment of fibroblasts can be, in part, attributed to the specific surface properties displayed by the polyester coating. As deduced from wettability spectrum determinations, the total surface free energy $\gamma_s$ of case films of the polyester is generally in the range of 40 to 50 dynes/cm. However, the predominant component of this surface force field is constituted by Van der Waals-London type dispersion forces, leading to a computable dispersion force component, $\gamma_s^d$ equal to 60% to 75% of the total $\gamma_s$. Thus, polar forces arising from H-bonding, dipole-dipole interactions, etc., represent the minor fraction of the total surface force field, leading to a computable polar force component, $\gamma_s^p$ equal to 25% to 50% of $\gamma_s$.

The surface characteristics deduced from wettability spectra are consistent with the results of Electron Spectroscopy for Chemical Analysis. These results have consistently indicated that the carbon/oxygen ratio, found within the 20 to 40 Å thick surface layer analyzed by ESCA, is appreciably greater than the stoichiometric carbon/oxygen ratio of the particular polyester. In these polyesters, most of the carbon atoms are present in $CH_3-$, $CH_2-$ and $CH=$ moieties, i.e., nonpolar groups capable of exerting only dispersion forces that contribute to the $\gamma_s^d$, whereas oxygen atoms are present in the carbonyl of ester groups which are potential H-bonding sites and contribute to the $\gamma_s^p$. The greater-than-stoichiometric carbon/oxygen ratio that was obtained by ESCA in the surface layer of these polyesters indicates a smaller abundance of oxygen-containing polar groups in the surface than the stoichiometric abundance of these groups in the bulk.

EXAMPLE 4

Figure 4:
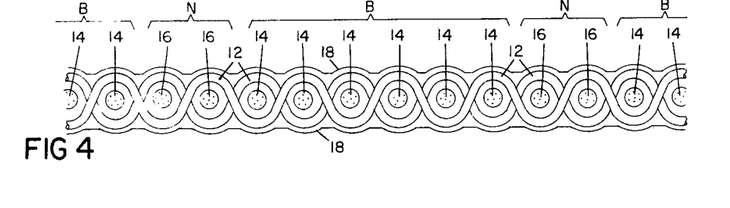
FIG. 4 is a diagram, similar to FIG. 2, illustrating aspects of still another vascular prosthesis in accordance with the invention.

An approximately seven centimeters long length of seven millimeter diameter tubing which was prepared to have a 75 percent bioresorbable cross yarn content as described in Example 2, was cleansed and subsequently overcoated with a 1:1 composite of poly(D,L-lactic acid) and poly(2,3-butylene succinate) under conditions identical to those described in Example 3 to provide coating 18 as indicated diagrammatically in FIG. 4. Implantation of this coated partially bioresorbable vascular graft into the right external carotid artery of a sheep was performed in the same manner as given above. As a control implanted into the left external carotid artery, a 75 percent bioresorbable cross yarn containing graft was used which had not been coated. Histopathological analyses of grafts, both of which were patent when excised after five weeks of indwelling time, indicated comparatively smoother pseudoneointimal linings on the luninal surface of the coated graft, as well as a comparatively milder tissue response on the external surface of the coated graft.

EXAMPLE 5

The in vivo performance characteristics of vascular grafts include, among others, the incidence of adherent thrombus formation potentially leading to occulusion, the rate of formation of neointimal lining, the interaction with perivascular tissues, etc. In a given species, these characteristics or, in general, graft healing and patency are known to be affected not only by the properties of a particular graft, but potentially by other factors as well, such as the implantation technique applied which can be a surgeon-dependent human factor. This example is to demonstrate that, if implanted in the same species via the same type of anastomoses by a different but equally competent surgeon, the results obtained with a coated woven graft are approximately the same as those described in Example 3.

Two 7.5 cm long pieces of an 8 mm diameter human-implantable grade, crimped, woven DeBakey-type vascular graft were coated as described in Example 3, except that double-precipitated poly(L-lactic acid) was used instead of poly(D,L-lactic acid). Each of these grafts was placed by end-to-end anastomoses into the right external carotid artery of each of two adult sheep under the same operative conditions as described in Example 1, but with all implantations performed by a different surgeon. Under identical conditions, each of two approximately 7.5 cm pieces of the same sterilized but uncoated graft were preclotted and placed into the left external carotid artery of the same animals during the same operations. After six weeks of indwelling time, all grafts were open to blood flow when both animals were electively terminated under conditions described in Example 1, and all grafts were excised. To within the limits of reproducibility of biological experiments, the condition of coated grafts and uncoated controls recovered from these implntations was, respectively, the same in terms of luminal lining and perivascular tissue response, as of those grafts which were recovered from the implantation experiment described in Example 3.

EXAMPLE 6

Another factor known to influence the in vivo performance characteristics of vascular grafts and especially, their so-called "healing" properties including, among others, the intensity of interactions with the blood stream and the rate of neointima fgormation, is the type of animal species used since the hematologic profile of different species are different. For example, the propensity of sheep blood for clotting induced by surfaces foreign to blood is somewhat less than that of canine blood, implying that, on these surfaces, canine blood clots easier. On the other hand, the fibrinolytic system that can dissolve clots as a result of lysis performed by certain blood enzymes, is weak or almost nonexistent in the sheep, whereas it is quite effective in dogs.

A piece of a 6 mm diameter human-implantable grade, crimped, woven DeBakey-type vascular graft which had been cleansed and coated as described in Example 5, was end-to-side anastomosed to the right external carotid artery of an approximately fifteen-kilogram, adult mongrel dog, under the operative conditions described in Example 1. With the two anastomoses separated by a distance of about 10 cm, the segment of the artery between them was tied off by ligatures. By simultaneous stretching and bending, the woven graft was shaped into an inverted "U" form such that it traversed through several layers of muscle, with the bottom of the loop brought close to the subdermis where blood flow through the graft could be easily detected by palpation or a Doppler flow meter. In an identical manner, a piece of the same human-implantable woven Dacron graft which had not been coated but was preclotted, was placed as a control into the left carotid artery of the same animal during the same operation.

After six weeks of indwelling time, both grafts were open to blood flow when the animal was electively terminated under conditions as described in Example 1, and the grafts were excised. The recovered coated graft displayed a smooth, white pseudoneointimal lining on its blood-contacting surface, whereas this lining in the uncoated control graft appeared to be in small patches which were interspersed with red thrombotic deposits partially occluding the graft lumen. In addition, during the indwelling period, a kink had evolved in the coated graft, for causes mostly attributable to the contraction of tissues the graft was tunnelled through.

While kinks, in general, give rise to the perturbation of flow and the formation of separated flow regions, the incidence of these flow phenomena in blood conduits which were made of material foreign to blood, is known to be a common hemodynamic cause of thrombus formation. In spite of the kink evolved, the luminal surface of the layer which was formed in this coated graft, was void of any adherent thrombus, indicating the dynamic in vivo hemocompatibility of that layer.

EXAMPLE 7

As a result of their fabric texture and comparatively smaller yarn density, vascular grafts knitted of multifiliament Dacron yarn are generally more conformable and compliant than grafts that were woven of the same yarn. For the same structural reasons, however, the porosity of knitted grafts is significantly greater. As measured in terms of leak rate at a constant pressure head of 100 mm Hg, the flow of water through a knitted graft can be typically on the order of 1,500 ml $cm^{-2}$ $min^{-1}$, whereas it is only about 150 ml $cm^{-2}$ $min^{-1}$ for woven grafts. To avoid large losses of blood, all types of currently available knitted grafts, without exception, must be sealed by preclotting prior to implantation.

A piece of an 8 mm diameter human-implantable grade, crimped, knitted Sauvage-type "Bionit" graft having a length of approximately 10 cm in the unstretched state, was cleansed ultrasonically and dried as described in Example 1. Using the apparatus and conditions described in Example 3, the graft was dipped twice into an acetonic solution of 2.5% by weight double precipitated poly(L-lactic acid) (approximately 75,000 Daltons weight-average molecular weight), 2.5% by weight double-precipitated poly(2,3-butylene succinate) (approximately 17,500 Daltons weight-average molecular weight) and 0.10% by weight triethyl citrate purified by vacuum fractionation. Following these initial dippings which served to deposit a thin coating over the individual yarns of the knitted fabric, the graft was dipped thrice more but in a moderately stretched state. This condition forces the polyester coating to form a continuous film between the individual yarns, covering over the interstitial space as shown, at a magnification of 200× in FIG. 5, a scanning electron micrograph (SEM) of the coated graft. If dip-coating of the knitted graft were to be continued without the conditions forcing this film formation, the graft can be sealed only by saturating its interstitial volume with the coating. This, however, results in the deposition of amounts of coating which convert the originally conformable graft into a rock-hard, brittle and nonconformant conduit ("steel pipe" effect). In contrast, the forced film formation disclosed here is manifested by the fact that, as seen from the SEM of the coated graft, the contours of most of the individual filaments are still discernible, indicative of the absence of saturation. The knitted graft that was coated according to this forced film formation technique essentially retains, in an aqueous environment and at body temperature, the original conformability of the same but uncoated graft. The amount of coating so deposited is sufficient to completely alleviate the need of preclotting, as substantiated by, among others, the experimentally established descrease of the original leak rate of 1,500 ml $cm^{-2}$ $min^{-1}$ of water to about 60 to 80 ml $cm^{-2}$ $min^{-1}$. Normalized to a unit length of 10 cm of graft in the unstretched state, the amount of polyester coating required to adequately seal, for example, an 8 mm diameter woven graft is in the range of 0.020 to 0.025 g, and on the order of 1.0 g for a knitted graft which has the same diameter and has been coated by the forced film formation technique.

Under operative conditions described in Example 1, an approximately twenty-kilogram mongrel dog was implanted in its right external carotid artery with an 8 mm diameter knitted Sauvage-type graft which had been coated by means of the forced film formation technique described above. Connections to the artery were accomplished by end-to-side anastomoses, and the graft was positioned in the inverted "U" form, in the same manner as described in Example 6. During the same operation but into the left external carotid artery of the same animal, a human-implantable grade, crimped, knitted Sauvage-type "Bionit" graft was placed in an identical manner as control, which was of the same diameter and approximately of the same length, and which had been sterilized only but not coated. The coated graft required no preclotting, whereas the uncoated graft could be preclotted only with difficulty since, according to standard implantation protocol, the animal was lightly anticoagulated with heparin.

After six weeks of indwelling time, both grafts were open to blood flow when the animal was electively terminated under conditions described in Example 1, and the grafts were excised. Microscopic histapathological examination revealed an advanced degree of neoendothelialization on the luminal surface of the coated knitted graft, whereas the luminal lining of the same but uncoated graft consisted mostly of fibrinaceous deposits.

While particular embodiments of the invention have been shown and described, various modifications will be apparent to those skilled in the art, and therefore it is not intended that the invention be limited to the disclosed embodiments or to details thereof and departures may be made therefrom within the spirit and scope of the invention.

What is claimed is:

1. A method of forming a prosthetic fabric device at least a portion of which is of a bioresorbable material whose surface properties favor fibroblast cell attachment and adhesion, and also encourage the infiltration of macrophages comprising the steps of dipping said device at a controlled rate into a solution of a bioresorbable, vasotropic effect inducing material, partial drying and inverting said device and redipping said device in said solution to form a bioresorbable coating on said device.

2. The method of claim 1 wherein said device is a fabric of bioresorbable and nonbioresorbable yarns.

3. The method of claim 2 and including after said redipping the further steps of stretching said coated fabric and dipping said stretched fabric in a solution of bioresorbable, vasotropic effect inducing material to form a prosthetic fabric article that has a leak rate of less than about 100 $cm^{-2}$ $min^{-1}$.

4. The method of claim 1 wherein said bioresorbable, vasotropic effect inducing material is a polyester derived from a Krebs-Cycle dicarboxylic acid and a metabolizable diol.

5. The method of claim 4 wherein said polyester is selected from the class consisting of poly(D,L-lactic acid) and poly(2,3-butylene succinate).

6. The method of claim 2 wherein the bioresorbable yarns are present in an amount of at least about 15%.

7. The method of claim 2 wherein the bioresorbable yarns are present in an amount of about 65% to 80%.

8. The method of claim 5 wherein the bioresorbable, vasotropic effect inducing material is a synthetic polymer.

9. The method of claim 5 wherein the bioresorbable, vasotropic effect inducing material is poly (D,L-lactic acid).

10. A method of forming a tubular vascular fabric prothesis at least a portion of which is of a bioresorbable material whose surface properties favor fibroblast cell attachment and adhesion, and also encourage the infiltration of macrophages comprising the steps of dipping said device at a controlled rate into a solution of synthetic bioresorbable, vasotropic effect inducing material partial drying inverting said device and redipping said device in said solution to form a bioresorbable coating on said device.

* * * * *

UNITED STATES PATENT AND TRADEMARK OFFICE
CERTIFICATE OF CORRECTION

PATENT NO. : 4,670,286

DATED : June 2, 1987

INVENTOR(S) : E. Nyilas et al.

It is certified that error appears in the above-identified patent and that said Letters Patent is hereby corrected as shown below:

Col. 1, line 13:   "stell" should read -- steel --.

Col. 2, line 13:   "caillary" should read -- capillary --.

Col. 5, line 15:   "significent" should read -- significant --.

Col. 8, line 47:   "FIGS. 3 and 5 are a scanning electron micrographs" should read --

Figure 5:
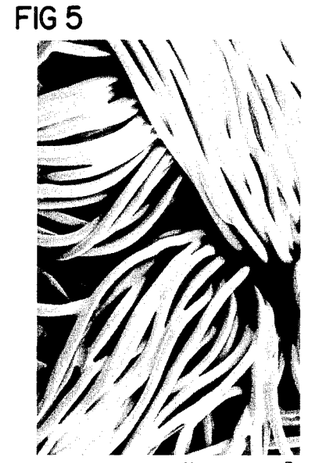

FIGS. 3 and 5 are scanning electron micrographs --.

Col. 11, line 21:  After "carbonyl" insert -- moiety --.

Col. 11, line 47:  "luninal" should read -- luminal --.

Col. 12, line 18:  "implntations" should read -- implantations --.

Col. 12, line 28:  "fgormation" should read -- formation --.

Col. 14, line 59:  "100 $cm^{-2} min^{-1}$" should read --

100 ml $cm^{-2} min^{-1}$ --.

UNITED STATES PATENT AND TRADEMARK OFFICE
CERTIFICATE OF CORRECTION

PATENT NO. : 4,670,286

DATED : June 2, 1987

INVENTOR(S) : E. Nyilas et al.

Page 2 of 2

It is certified that error appears in the above-identified patent and that said Letters Patent is hereby corrected as shown below:

Col. 16, line 5: After "material" insert a comma.

Col. 16, line 6: After "drying" insert a comma.

Signed and Sealed this

Seventeenth Day of November, 1987

Attest:

DONALD J. QUIGG

Attesting Officer

Commissioner of Patents and Trademarks